(12) United States Patent
Nakai et al.

(10) Patent No.: US 10,190,956 B2
(45) Date of Patent: Jan. 29, 2019

(54) TRUE DENSITY MEASUREMENT DEVICE

(71) Applicant: MicrotracBEL Corp., Osaka (JP)

(72) Inventors: Kazuyuki Nakai, Osaka (JP); Hiromi Yamazaki, Osaka (JP); Kaori Nakamura, Osaka (JP); Takayuki Goumoto, Osaka (JP)

(73) Assignee: MicrotracBEL Corp., Osaka (JP)

( * ) Notice: Subject to any disclaimer, the term of this patent is extended or adjusted under 35 U.S.C. 154(b) by 198 days.

(21) Appl. No.: 15/113,029

(22) PCT Filed: Jan. 22, 2015

(86) PCT No.: PCT/JP2015/051662
§ 371 (c)(1),
(2) Date: Jul. 20, 2016

(87) PCT Pub. No.: WO2015/111651
PCT Pub. Date: Jul. 30, 2015

(65) Prior Publication Data
US 2017/0030817 A1   Feb. 2, 2017

(30) Foreign Application Priority Data
Jan. 23, 2014 (JP) ................................ 2014-010211

(51) Int. Cl.
*G01N 9/26* (2006.01)
*G01N 9/02* (2006.01)

(52) U.S. Cl.
CPC ................. *G01N 9/26* (2013.01); *G01N 9/02* (2013.01); *G01N 2009/028* (2013.01)

(58) Field of Classification Search
CPC ............. G01N 9/00; G01N 9/26; G01N 9/266
USPC ............. 73/23.28, 30.01, 30.02, 30.04, 32 R
See application file for complete search history.

(56) References Cited

U.S. PATENT DOCUMENTS

| 2,667,782 A | 2/1954 | Shea |
| 3,241,361 A | 3/1966 | Broughton |
| 4,083,228 A | 4/1978 | Turner et al. |
| 5,074,146 A | 12/1991 | Orr et al. |
| 5,583,897 A | 12/1996 | Hill |

(Continued)

FOREIGN PATENT DOCUMENTS

| CN | 101910820 A | 12/2010 |
| DE | 102007025067 A1 | 12/2007 |

(Continued)

OTHER PUBLICATIONS

International Search Report and Written Opinion received in PCT/JP2015/051662 dated Apr. 21, 2015 (with English translation).

(Continued)

*Primary Examiner* — Benjamin R Schmitt
(74) *Attorney, Agent, or Firm* — Dorsey & Whitney, LLP

(57) ABSTRACT

This true density measurement device is a device that is used to measure the true density of a sample by a gas phase substitution method, and is provided with: a sample chamber for accommodating the sample, the sample chamber being pressurized through the introduction of an inert gas; and an expansion chamber into which is released the inert gas filling the sample chamber. The expansion chamber under conditions of normal use, is opened and closed by a detachable cover, and the volume thereof is modified by insertion or withdrawal of a volume modification member.

4 Claims, 12 Drawing Sheets

(56) References Cited

U.S. PATENT DOCUMENTS

| | | |
|---|---|---|
| 2003/0121321 A1 | 7/2003 | Dempster et al. |
| 2010/0269577 A1 | 10/2010 | Jorion et al. |
| 2017/0010196 A1 | 1/2017 | Nakai et al. |

FOREIGN PATENT DOCUMENTS

| | | |
|---|---|---|
| EP | 0720011 A1 | 7/1996 |
| JP | S40-026644 Y | 9/1965 |
| JP | S49-134316 U | 11/1974 |
| JP | S55-134079 A | 10/1980 |
| JP | 06-307910 A | 11/1994 |
| JP | 09-133625 A | 5/1997 |
| JP | 9-255087 A | 9/1997 |
| JP | 2009-002824 A | 1/2009 |
| JP | 2011-508230 A | 3/2011 |

OTHER PUBLICATIONS

Extended European Search Report received in PCT/JP2015051662, dated Jul. 26, 2017.

Notice of Grounds for Rejection received in JP App. No. 2014-010211 dated Dec. 1, 2015.

English Translation of Office Action dated Aug. 22, 2018 for Chinese application No. 2015800056688.

US 10,190,956 B2

TRUE DENSITY MEASUREMENT DEVICE

RELATED APPLICATIONS

This application is a 371 National Stage application claiming priority to PCT Application No. PCT/JP2015/051662, filed Jan. 22, 2015, which claims priority to Japanese Patent Application No. 2014-010211 filed on Jan. 23, 2014, which applications are incorporated herein by reference in their entirety, for any purpose.

TECHNICAL FIELD

The present invention relates to a true density measurement device for measuring the true density of an object to be measured with a gas phase substitution method.

BACKGROUND ART

In measurement of a true density using a gas phase substitution method, a sample chamber in which an object to be measured is housed is filled with an inert gas, such as He gas, and the inert gas is subsequently released into an expansion chamber, to find the volume of the object to be measured based on a change in an internal pressure of the sample chamber resulting from the release, and convert the found volume of the object to be measured into a true density. A concrete method for measurement is specified in Japanese Industrial Standard (JIS) Z8807.

As a true density measurement device based on the gas phase substitution method, for example, a device disclosed in Patent Document 1 has been known. The device of Patent Document 1 employs no arrangement for allowing the capacity of an expansion chamber to be changed.

CITATION LIST

Patent Literature

Patent Document 1: U.S. Pat. No. 5,074,146

SUMMARY

Technical Problem

In conventional true density measurement devices, an arrangement has been employed with which the capacity of a sample chamber can be changed depending on the volume of an object to be measured or other factors. Although this allows measurement with high accuracy to be performed on various objects to be measured, it is still desired for the true density measurement devices to be further improved in their accuracy of measurement.

Solution to Problem

A true density measurement device for measuring the true density of an object to be measured with a gas phase substitution method according to an aspect of the present invention includes a sample chamber that is configured to house the object to be measured and is pressurized by introducing an inert gas into the sample chamber, and an expansion chamber into which the inert gas having been introduced into the sample chamber is released, in which the expansion chamber is opened and closed by a lid that can be attached or detached under normal usage conditions, and has a variable capacity that is changed by inserting or removing a capacity changing member.

According to the true density measurement device in the aspect of the present invention, the expansion chamber can be accessed in an easy way, and the capacity of the expansion chamber can be changed through an easy and simple operator's action of inserting or removing the capacity changing member. In this way, various objects to be measured can be measured with a higher degree of accuracy. Further, according to the true density measurement device in the aspect of the present invention, the accuracy of measurement can be greatly improved without yielding disadvantages of upsizing the device, increasing costs, and the like.

DESCRIPTION OF EMBODIMENTS

Figure 1:
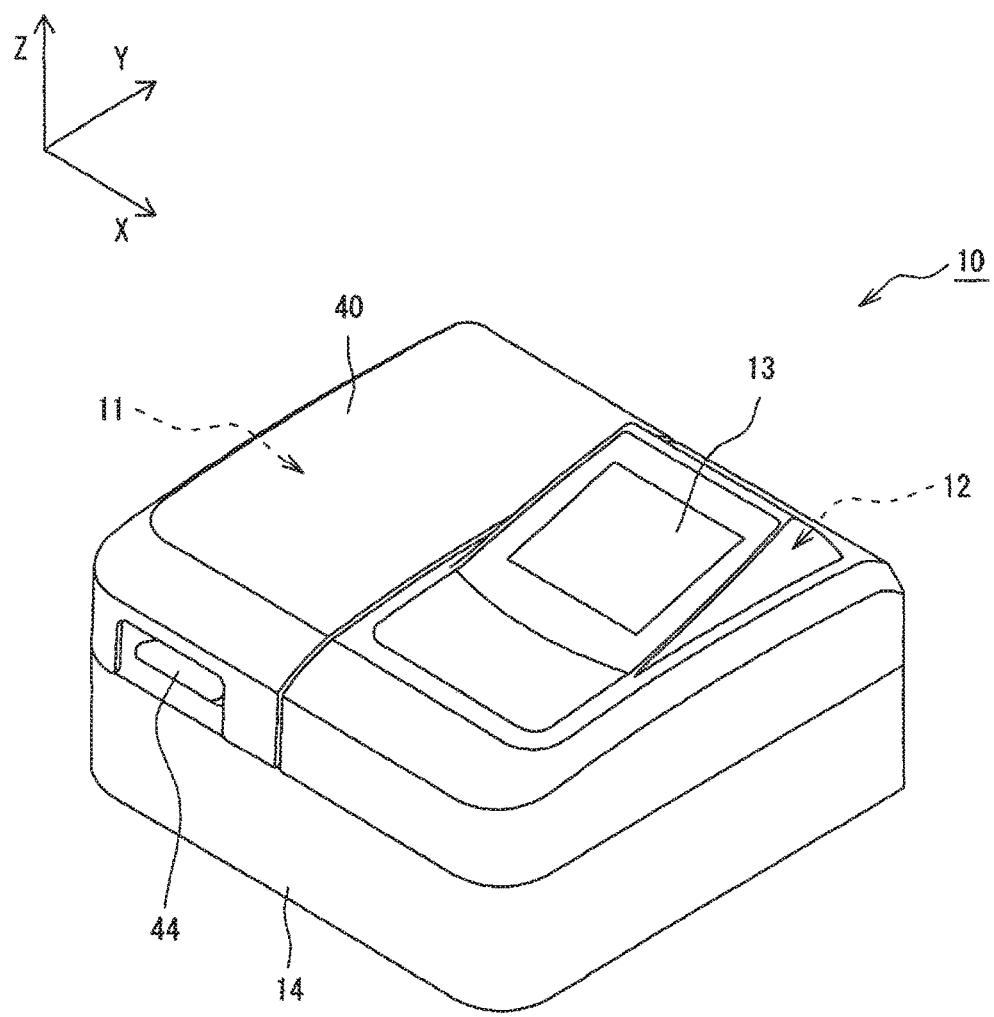
FIG. 1 is a diagram showing an outer appearance of a true density measurement device as an example of an embodiment.

The present inventors have devised a way of allowing the capacity of an expansion chamber to be changed, and therefore achieved a further increase in accuracy of measurement. Because access to the expansion chamber is facilitated, the capacity of the expansion chamber can be changed through an easy and simple action of an operator, such as insertion or removal of a capacity changing member. This has contributed to significant improvement in accuracy of measurement without having detrimental effects of upsizing the device and increasing costs.

In the true density measurement device, which is one example of an embodiment, the expansion chamber is open in the same as orientation that of a sample chamber.

The true density measurement device, which is one example of the embodiment, includes a block in which the sample chamber and the expansion chamber are provided, and both openings of the expansion chamber and the sample chamber are defined on an upper surface of the block.

In the true density measurement device, which is one example of the embodiment, the expansion chamber has a maximum capacity that is substantially equal to that of the sample chamber.

The true density measurement device, which is one example of the embodiment, includes a notifying section that recommends the use of the capacity changing member based on a relationship between a previously obtained capacity of the expansion chamber and measurement errors.

Referring to the drawings, a true density measurement device 10 which is one example of the embodiment will be described in detail. The true density measurement device 10 is explained merely as an example of the embodiment, and application of the present invention is not limited to the example. Further, the drawings referenced in the embodiment are schematically illustrated, and a scaling factor of dimensions and other details of the components illustrated in the drawings are not necessarily the same as those of an actual device. Specific dimension ratios and other details should be determined in consideration with the following explanations.

Hereinafter, terms representing directions, such as a vertical direction, a left and right direction, and a front and rear direction, are used for convenience of explanation. In particular, the direction indicated by an arrow X in FIG. 1 is defined as the left and right direction or a width direction of the true density measurement device 10 (the arrow head is pointed to the right), the direction indicated by an arrow Y is defined as the front and rear direction or a depth direction (the arrow head is pointed to the rear), and the direction indicated by an arrow Z is defined as the vertical direction (the arrow head is pointed to the top). In addition, the terms "approximately", "substantially", "nearly", etc. are used herein with the intention to imply that substantially identical instances, for example, embrace both completely identical and almost identical ones.

Referring to FIGS. 1 to 7, the structure of the true density measurement device 10 will be described in detail.

Figure 2:
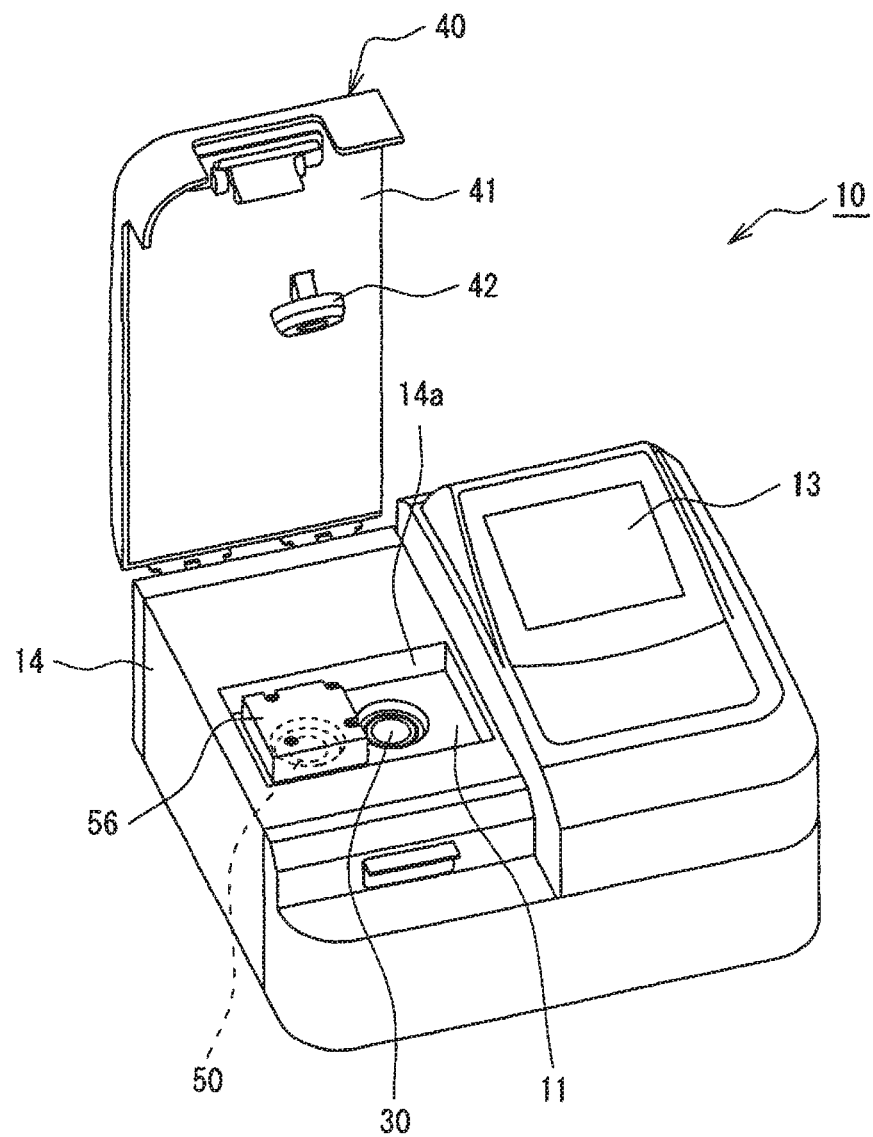
FIG. 2 is a diagram showing, in an opened state, a sample chamber in the true density measurement device according to the example of the embodiment.

FIGS. 1 and 2 are drawings showing the outer appearance of the true density measurement device 10, in which FIG. 2 shows a state where a lid unit 40 is lifted up to open a sample chamber 30. The true density measurement device 10 is a device for measuring the true density of an object to be measured with a gas phase substitution method, and is equipped with a manifold 11 that includes the sample chamber 30, an expansion chamber 50, and other components, a control unit 12 for controlling the manifold 11 and other components, calculating measurement values, and performing other operations, and a touch panel 13. The touch panel 13 functions as a display unit for displaying measured results and the like and also functions as an operation unit used for inputting measurement conditions and the like. Note that the display unit and the operation unit may be separately provided.

The true density measured by the true density measurement device 10 is a density that is used for volume to density conversion of a volume occupied by an object to be measured. The gas phase substitution method, which is also referred to as a fixed volume expansion method, is a measurement method using Boyle's law related to the volume and pressure of a gas under a condition of constant temperature, as will be described in detail below. The object to be measured is not specifically limited. The true density measurement device 10 is applicable to various substances, such as solid matter, powder, slurry, and liquids. In the embodiment, a sample 100 of powder is used by way of illustration as the object to be measured (refer to FIG. 7 and elsewhere).

The true density measurement device 10 has a case 14 that covers the manifold 11 and the control unit 12. In the true density measurement device 10, the manifold 11 is housed, for example, in the left half of the case 14, while the control unit 12 is housed in the right half of the case 14. The case 14 has a case opening 14a at a position corresponding to locations of the sample chamber 30 and the expansion chamber 50 in the manifold 11. This allows the sample chamber 30 and the expansion chamber 50 to be accessed without disassembling the case 14. In a case where the expansion chamber 50 is not frequently accessed, the expansion chamber 50 may be closed by a cover. In this case, however, it is also required that the cover be easily detached without disassembling the device.

The true density measurement device 10 has the lid unit 40. The lid unit 40 includes a lid unit body 41 (hereinafter simply referred to as a "body 41") and a lid 42 for hermetically sealing the sample chamber 30. The body 41 is configured, as described in detail below, to function as an arm used for operations to open and close the lid 42. The lid 42 is swingably attached to the body 41, and the stroke of a swing may be set to a very small value as long as the components are manufactured with high precision. The body 41 has a depth dimension that is substantially equal to a depth dimension of the case 14 and a width dimension that is substantially a half of a width dimension of the case 14. The body 41 is pivotally supported on the case 14, and is designed to cover, when the lid unit 40 is closed, a portion of the manifold 11 that is exposed from the case opening 14a of the case 14. The expansion chamber 50 is hermetically sealed by another lid 56 separate from the lid unit 40.

Figure 3:
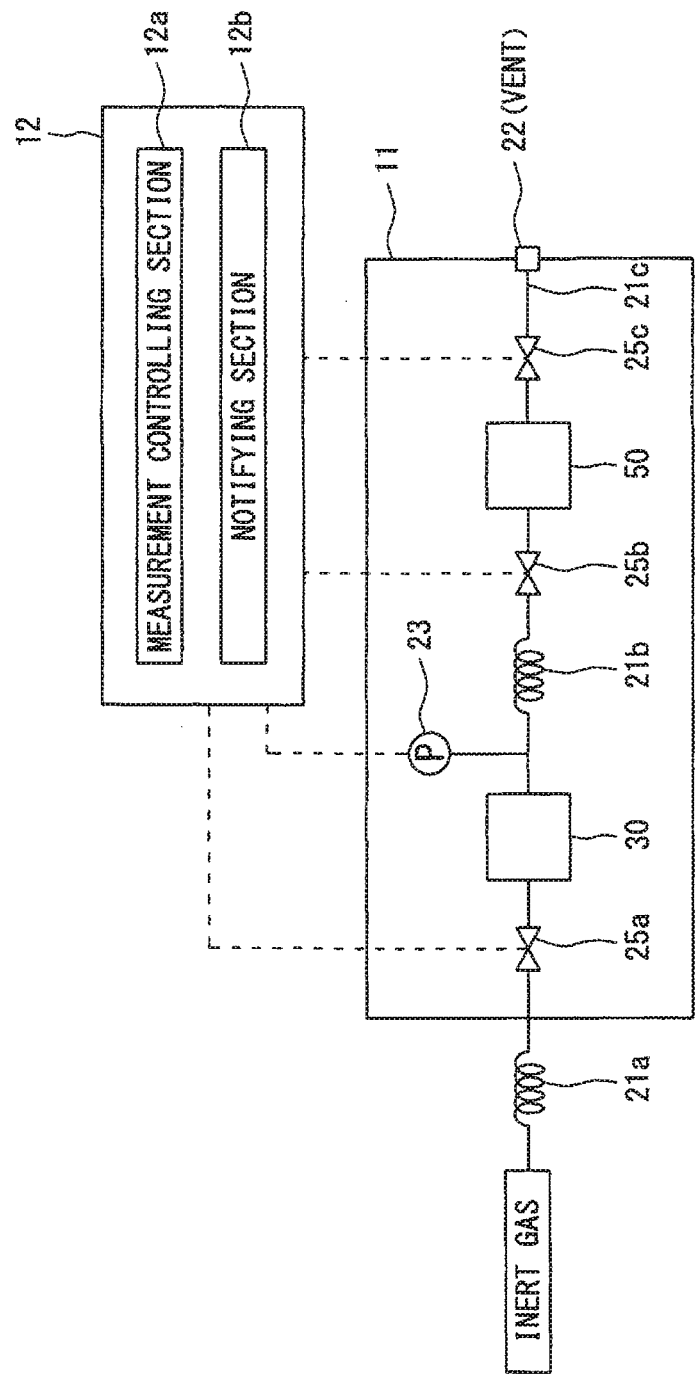
FIG. 3 is a block diagram for explaining structure of the true density measurement device according to the example of the embodiment.
Figure 4:
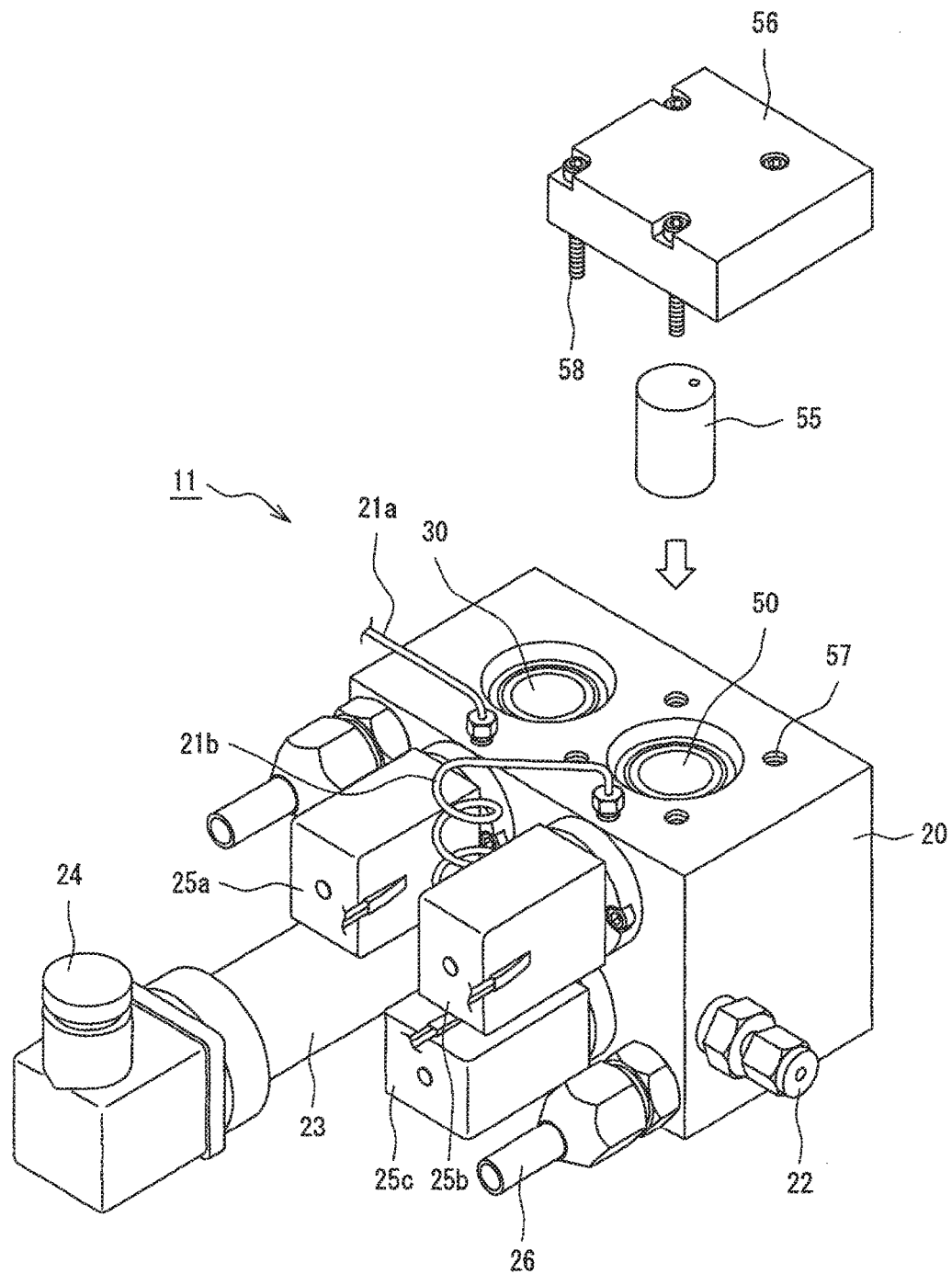
FIG. 4 is a diagram showing an outer appearance of a manifold in the true density measurement device according to the example of the embodiment.

FIG. 3 is a block diagram for explaining the structure of the true density measurement device 10 (in particular, the structure of the manifold 11). FIG. 4 shows the outer appearance of the manifold 11. The manifold 11 has a block 20 in which the sample chamber 30 and the expansion chamber 50 are defined. Although the sample chamber 30 and the expansion chamber 50 may be placed on either side in the left and right direction, it is assumed in the present embodiment that the sample chamber 30 is located on an inert gas introduction side. In addition, the manifold 11 further includes gas pipes 21a, 21b, and 21c which are attached to the block 20, a vent 22, a pressure detector 23, solenoid valves 25a, 25b, and 25c, and other components. In the true density measurement device 10, the manifold 11 is arranged in such a manner that the pressure detector 23 and the solenoid valves are located on a device rear side behind the block 20.

The block 20 has a substantially rectangular shape whose sides along the width direction are slightly longer than those along the depth direction. In the block 20, the sample chamber 30 and the expansion chamber 50 are placed side by side in the width direction. Preferably, the block 20 is formed of a metallic material, such as aluminum, in light of temperature uniformity in the two chambers. Further, a constant temperature water feeder 26 may be mounted on the block 20 to circulate constant temperature water (supplied from a not-illustrated constant temperature bath) through the block 20, and/or the block 20 may be covered with a heat insulating material. In place of the constant temperature water feeder 26, a temperature control mechanism including a heater, a Peltier device, a temperature sensing element, a controller, etc. may be incorporated.

The gas pipe 21a is a pipe for connecting an inert gas source, such as a not-illustrated He gas cylinder, to the sample chamber 30. The gas pipe 21a is opened and closed by the solenoid valve 25a. The gas pipe 21b is a pipe for connecting the sample chamber 30 to the expansion chamber 50, and is opened and closed by the solenoid valve 25b. To prevent the sample 100 from scattering, the gas pipes 21a and 21b are preferably composed of a so-called resistance pipe, such as a pipe of small inner diameter or a coil shaped pipe. The gas pipe 21c is a pip, for connecting the expansion chamber 50 to the vent 22, and is opened and closed by the solenoid valve 25e.

The pressure detector 23 is a device for detecting pressures of the sample chamber 30 and the expansion chamber 50. Based on detected values from the pressure detector 23, for example, the control unit 12 calculates a true density of the sample 100. The pressure detector 23 is equipped with a connector 24 for outputting the detected values to the control unit 12. The pressure detector 23 is attached to the gas pipe 21b for connecting the sample chamber 30 to the expansion chamber 50 at a location closer to the sample chamber 30 than the solenoid valve 25b.

The sample chamber 30 and the expansion chamber 50 are, as described above, connected to each other by the gas pipe 21b to which the pressure detector 23 and the solenoid valve 25b are attached. The sample chamber 30 is a chamber for housing the sample 100, and is pressurized by introducing the inert gas, such as He gas, to the sample chamber 30 at the time of measurement of the true density. The sample chamber 30 has a variable capacity that can be changed by replacing a below-described sample container with another sample container of a different type. The expansion chamber 50 is a chamber into which the inert gas that has been introduced into the sample chamber 30 is released. Further, the expansion chamber 50 is opened and closed by the lid 56 which can be attached or detached under normal usage conditions, and has a variable capacity that can be changed by inserting or removing a capacity changing member 55. The inert gas within the sample chamber 30 is directed into the expansion chamber 50 by opening the solenoid valve 25b.

A measurement of the true density is performed by the true density measurement device 10 in a procedure described below. A method for the measurement is a conventional method that has been publicly known and specified in JIS Z 8807. A series of procedural steps, such as opening and closing of each solenoid valve and calculation of the true density, are performed by a measurement controlling section 12a in the control unit 12. The steps are as follows.

(1) The sample 100 having an unknown volume is housed in the sample chamber 30, the lid 42 is closed, and the solenoid valve 25a is opened to introduce the He gas having a known pressure into the sample chamber 30. As a result, pores in the sample 100 are filled with the He gas. In this state, the pressure of the He gas filled in the sample chamber 30 is measured.

(2) Then, the solenoid valve 25b is opened to release the He gas filled in the sample chamber 30 into the expansion chamber 50 which is hermetically sealed by the lid 56. This allows the He gas filled in an internal space other than the sample 100 in the sample chamber 30 to be diffused throughout the two chambers. In this state, the pressure is measured again to find the pressure of the He gas after the He gas is introduced into the expansion chamber 50.

(3) Because the capacities of the sample chamber 30 and the expansion chamber 50 are known, the volume of the sample 100 can be obtained from a change in pressure resulting from diffusion of the He gas. The true density of the sample 100 is calculated based on both a previously measured weight of the sample 100 and the change in pressure.

The requirements of the sample chamber 30 include reproducibility of its capacity during repeated measurements. Although the capacity of the sample chamber 30 can be calibrated by means of a reference sphere whose volume is previously verified, the calibration is not performed for each measurement. Because of this, a property of stability is required of the sample chamber 30. Having the property of stability between the calibration and a measurement is indispensable. In a case of the present embodiment, because a range encircled by a below-described O ring 34 is counted as the capacity of the sample chamber 30, it is necessary to close the lid 42 in the same state every time. For example, a margin of error allowed in the vertical direction when the lid 42 is pressed against the circumferential edge region around the opening 31 is in the order of a few μm (under a condition where a target degree of reproducibility of measurement is set to 0.01%). This secures the reproducibility of the sample chamber capacity. In addition, because the sample chamber 30 is opened and closed every time the sample 100 is replaced, it is required for a mechanism of opening and closing the sample chamber 30 to have a feature of being easy to open and close, in addition to the reproducibility. As described below, according to the opening and closing mechanism in the true density measurement device 10, both excellent reproducibility of the sample chamber capacity and a favorable opening and closing feature of the lid 42 can be obtained.

Figure 5:
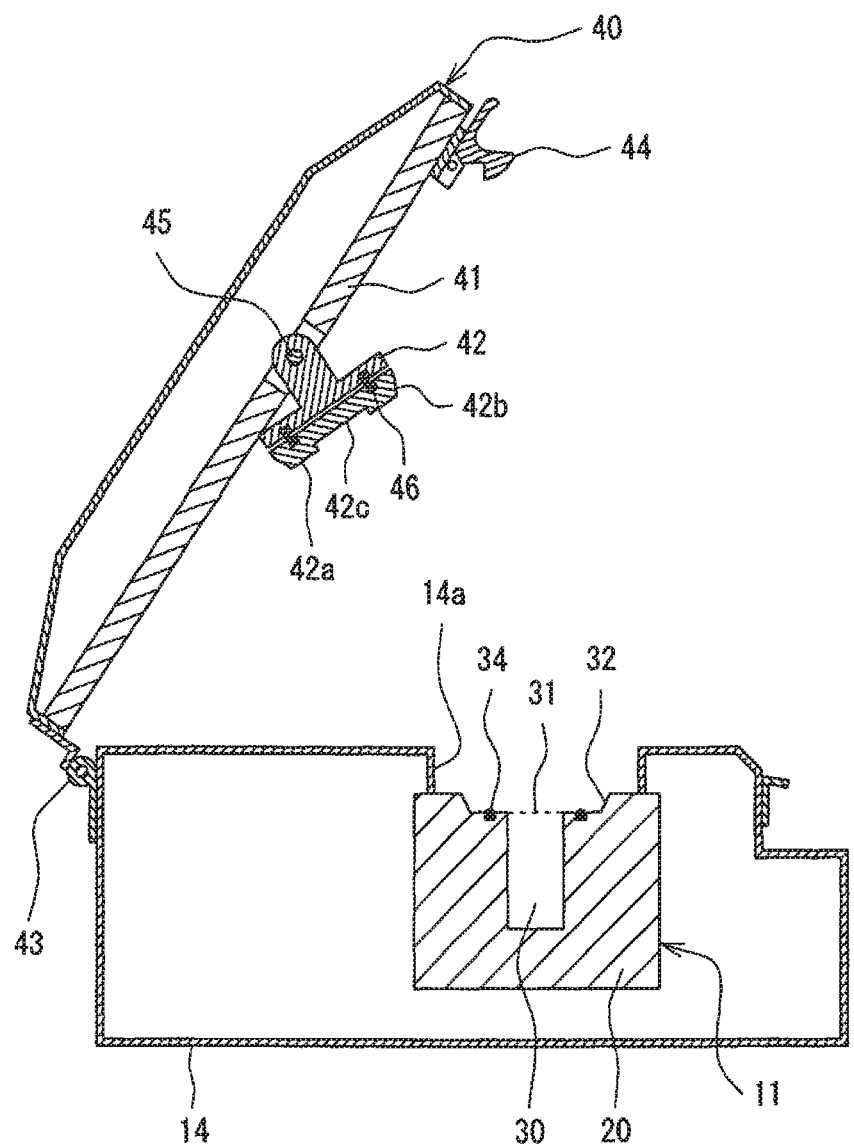
FIG. 5 is a diagram showing, in cross section taken along a depth direction, a part of the true density measurement device according to the example of the embodiment.
Figure 6:
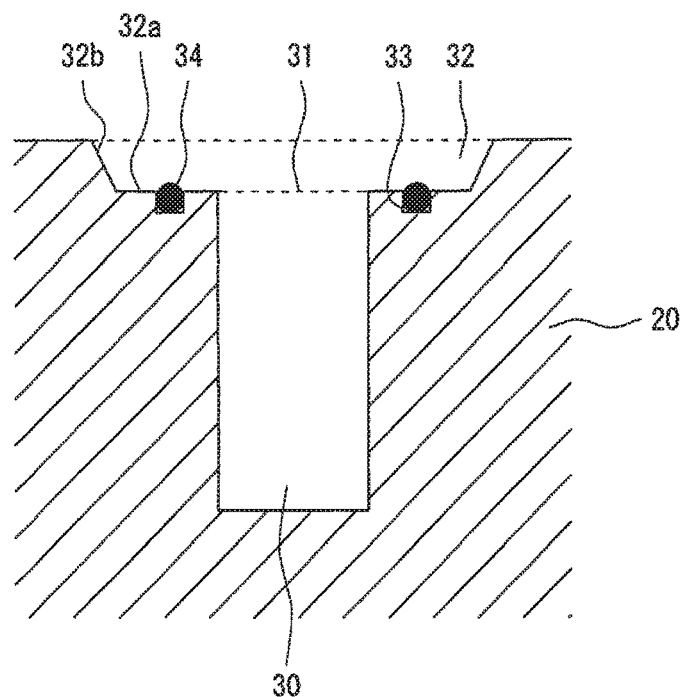
FIG. 6 is an enlarged cross sectional view showing the sample chamber and the vicinity of an opening in the true density measurement device according to the example of the embodiment.
Figure 7:
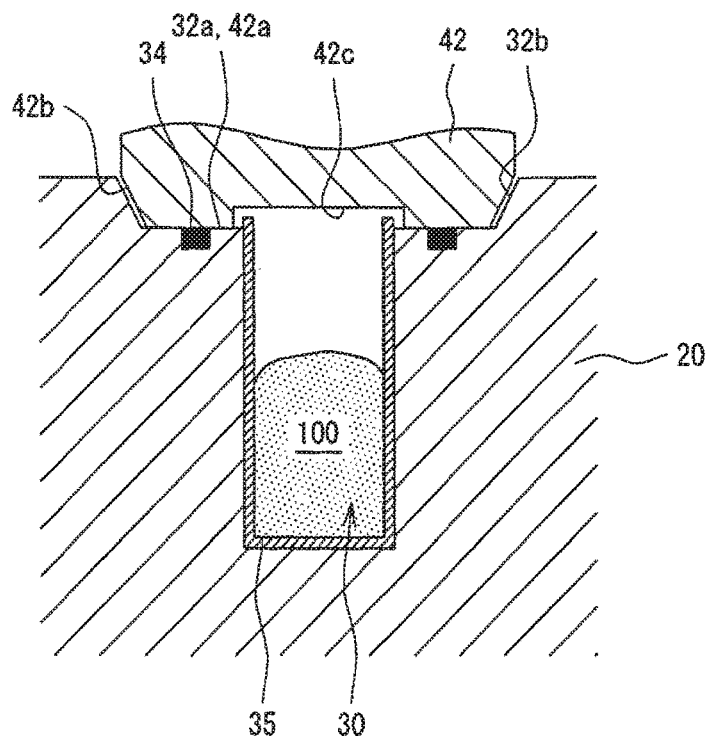
FIG. 7 is an enlarged cross sectional view showing the sample chamber and the vicinity of the opening in the true density measurement device according to the example of the embodiment, in a state where the sample chamber is hermetically sealed by a lid.

Next, further referring to FIGS. 5 to 7, the structure of the sample chamber 30 and the lid unit 40, in particular, the mechanism of opening and closing the sample chamber 30, will be described in detail. FIG. 5 is a diagram showing a part of the true density measurement device 10 in cross section taken along the depth direction. FIGS. 6 and 7 are enlarged cross sectional views showing the sample chamber 30 and the vicinity of the opening 31. FIG. 7 shows a state where the sample chamber 30 is hermetically sealed by the lid 42.

The sample chamber 30 is a recessed part extending downward from an upper surface of the block 20, and has an internal space in which the sample 100 is housed. Preferably, the sample chamber 30 has the shape of a nearly perfect circle in cross section taken along the width direction, and has a diameter which is kept substantially constant in a length (vertical) direction. Note that the size and other dimensions of the sample chamber 30 may be established as appropriate. For example, the sample chamber 30 may be defined to have a diameter of approximately 1 to 10 cm, a length of approximately 1 to 10 cm, and an internal space size (capacity) of approximately 0.1 to 2000 ml.

The sample chamber 30 is, as described above, the recessed part formed from the upper surface of the block 20 and is opened upward. In other words, the opening 31 of the sample chamber 30 is defined on the upper surface of the block 20. In this way, the sample 100 can be easily loaded and unloaded. The sample 100 is housed in the sample chamber 30 with, for example, a sample container 35 shaped like a cylinder with a bottom, in which the sample 100 is loaded. The diameter of the sample container 35 is defined to be as close to the diameter of the sample chamber 30 as possible to the extent that insertion and removal are not hindered. When a degassing channel is provided in a sample chamber wall in the block 20, it becomes easier to insert and remove the sample container 35. The sample container 35 is designed to have a length slightly greater than the length of the sample chamber 30, which causes an upper end of the sample container 35 to be upwardly protruded from the opening 31 of the sample chamber 30. For this reason, a recessed part 42c is formed on a bottom surface 42a of the lid 42.

A loading amount of the sample 100 is appropriately selected depending on a level of sample value, a measurement accuracy, and other factors. In a case where the sample 100 is of high value, there is a desire to minimize the loading amount. When the capacity of the sample chamber 30 (space which is not occupied by the sample) is too great relative to the amount of sample, the accuracy of measurement is decreased. More specifically, because the accuracy is deteriorated when measured values are close to a lower extremity in a measurable range of the pressure detector 23, it is desirable that the capacity of the sample chamber 30 is small in a case where the amount of sample is small.

The capacity of the sample chamber 30 can be changed using the sample container or other components. This enables a single device to measure various types of samples. For example, when an instance of using the sample container 35 illustrated in FIG. 7 is compared with an instance of using a below-described sample container 35z illustrated in FIG. 8, the sample chamber capacity can be smaller in the latter case. Alternatively, the sample chamber capacity may be changed by means of a separate member that is used in conjunction with the sample container.

The sample chamber 30 is hermetically sealed by the lid 42 which is pressed against the circumferential edge region around the opening 31. The circumferential edge region around the opening 31 includes the recessed part 32 into which the lid 42 is fitted. The recessed part 32 has a function of guiding the lid 42 to an appropriate position. The recessed part 32 is formed from the uppermost surface of the block 20 so as to have a depth of, for example, approximately 1 to 30 mm, and the opening 31 is defined in the bottom surface 32a of the recessed part 32. In other words, the opening 31 is downwardly retreated from the uppermost surface of the block 20 by an amount corresponding to the depth of the recessed part 32. The lid 42 blocks the opening 31 when the bottom surface 42a of the lid 42 is pressed against the bottom surface 32a of the recessed part 32. For this reason, the bottom surfaces 32a and 42a are substantially flat in regions other than where the below-described groove 33 and the recessed part 42c are formed. Preferably, the opening 31 is formed at an approximate center of the bottom surface 32a of the recessed part 32.

The recessed part 32 has the shape of a substantially perfect circle in cross section taken along the width direction, and has a diameter which is decreased toward the bottom surface 32a. In other words, the recessed part 32 is in the shape of a substantially perfect circle on the bottom surface 32a, and has a side surface 32b which is inclined so that the diameter is decreased from the uppermost surface of the block 20 toward the sample chamber 30. Similarly, the lid 42 is in the shape of a substantially perfect circle on the bottom surface 42a, and has a side surface 42b which is inclined so as to decrease the diameter toward the sample chamber 30 in a region fitted into the recessed part 32. Formation of such tapered side surfaces enables the lid 42 to be easily fitted at an appropriate location in an appropriate state. Taking into account airtightness of the sample chamber 30, the feature of guiding the lid 42, and other factors, the diameter of the bottom surface 32a is preferably greater than that of the bottom surface 42a, and also preferably, inclination angles of the side surfaces 32b and 42b are substantially equal to each other.

As will be described in detail below, the lid 42 is a non-rotary lid which is not rotated along a circumferential direction of the opening 31. For this reason, no flutes or other features for mutual engagement are formed on the side surfaces or other regions of the lid 42 and the recessed part 32. In addition, it is preferably defined that (the diameter of the bottom surface 32a)>(the diameter of the bottom surface 42a) and (the inclination angle of the side surface 32b)≈(the inclination angle of the side surface 42b) to prevent the side surfaces 32b and 42b from contacting with each other when the bottom surface 42a is pressed against the bottom surface 32a with the centers of the bottom surfaces 32a and 42a being substantially aligned (refer to FIG. 7). In other words, a predetermined clearance is created between the side surfaces 32b and 42b. The predetermined clearance is preferably defined within a range that does not cause the recessed part 42c formed on the bottom surface 42a to rest on the below-described O ring 34 and does not allow the bottom surface 42a to touch the sample container 35 even though the center of the bottom surface 42a is displaced from the center of the bottom surface 32a.

The groove 33 is formed at a position that encircles the opening 31 in the bottom surface 32a of the recessed part 32. The groove 33 is preferably formed in the shape of a substantially perfect circle about the opening 31. The O ring 34 functioning as a sealing member is fitted into the groove 33. The depth of the groove 33 is set preferably to 70%-92% or more preferably to 75%-85% of a wire diameter of the O ring 34. That is, the O ring 34 is projected from the bottom surface 32a by an amount equivalent to preferably 8% to 30%, or more preferably 15% to 25%, of the wire diameter (refer to FIG. 6). Preferably, the groove 33 is shaped like a letter U in cross section, and the width of the groove 33 is substantially equal to the wire diameter of the O ring 34. It is preferable in terms of a smaller dead capacity that the diameter of the groove 33 (the diameter of the O ring 34) is as small as possible in a range that does not impair airtightness of the sample chamber 30 and other features. In other words, the groove 33 into which the O ring 34 is fitted is preferably located as close to the opening 31 as possible.

The O ring 34 is fitted, as described above, in the groove 33 with a part of the O ring 34 protruded from the bottom surface 32a. In a state of being squashed by the lid 42, the O ring 34 secures airtightness of the sample chamber 30 encircled by the O ring 34 (refer to FIG. 7). The O ring 34 is squashed until the bottom surface 42a of the lid 42 makes contact with the bottom surface 32a of the recessed part 32, i.e. until reaching a state where the O ring 34 is no longer projected from the bottom surface 32a. The wire diameter of the O ring 34 is, for example, no greater than 2.0 mm or no greater than 1.5 mm. When the O ring 34 whose wire diameter is limited as described above is used, a necessary pressing pressure can be minimized without impairing the airtightness. JIS O rings of No. S24 may be used for the O ring 34.

The O ring 34 is not lubricated with a lubricant such as grease. Because the lid 42 simply presses the O ring 34 from above rather than being rotated on the O ring 34, no strong rotary force is exerted on the O ring 34, which can eliminate the necessity of applying grease. Accordingly, the true density measurement device 10 does not suffer from the presence of contamination of the sample chamber 30 and measurement errors caused by grease. It should be noted that such an O ring may be provided on the bottom surface 42a of the lid 42. In this case, a groove into which the O ring is fitted may be formed at a position that encircles the recessed part 42c on the bottom surface 42a.

The lid unit 40 includes, as described above, the body 41 which functions as an operation arm and the non-rotational 42 which is swingably attached to the body 41. The body 41 is pivotally attached to the case 14 in a position capable of being lifted from the front side toward the rear side of the device. The body 41 is operated at a front end part (hereinafter referred to as a "first end part"), and pivoted about a rear end part (hereinafter referred to as a "second end part"). The lid 42 is mounted between the first and second end parts of the body 41. The lid 42 is pressed against the bottom surface 32a of the recessed part 32 which is the circumferential edge region around the opening 31 by pushing down the first end part of the body 41, to hermetically seal the sample chamber 30. In this way, the sample chamber 30 can be opened and closed through a simple and easy operation of pushing down or lifting up the first end part of the body 41.

The body 41 functions as a lever that takes the first end part as the point of effort, the second end part as the fulcrum, and a position where the lid 42 is attached as the point of load. Therefore, the O ring 34 can be squashed with a small force to hermetically seal the sample chamber 30. Although the lid 42 is attached in this embodiment at the position which is slightly nearer to the point of effort than to the fulcrum, the position of attaching the lid 42 may be shifted toward the fulcrum when a greater pressing force is needed. In this case, the manifold 11 is placed in a position, for example, where the pressure detector 23 is arranged on a device front side relative to the block 20. Alternatively, a double lever mechanism may be applied to the body 41.

The body 41 is pivotally supported through a support unit 43 by the case 14. Although the structure of the support unit 43 is not specifically limited as long as the support unit 43 can pivotally support the body 41, it is preferable in terms of good operability that the support unit 43 is composed of a torque hinge which enables the body 41 to be retained in a specific lifted position. The torque hinge is attached to the second end part of the body 41 and to the rear end of the case 14 in such a manner that the axis of rotation of the torque hinge is aligned with the width direction.

The body 41 is fixed by a fixture unit 44 in a state where the lid 42 is pressed against the circumferential edge region around the opening 31, i.e. a state where the first end part is pushed down. The structure of the fixture unit 44 is not specifically limited as long as the fixture unit 44 can fix the body 41 in the state where the first end part is pushed down. For example, the fixture unit 44 may be composed of a lever latch. In the lever latch, for example, a lever part is attached to the first end part of the body 41 while a receiver seat is attached to the front end of the case 14, with the axis of rotation of the lever part being aligned with the width direction.

The lid 42 is swingably mounted between the first and second end parts of the body 41 by means of a floating joint 45. The floating joint 45 allows the lid 42 to swing at least along the front and rear direction. Although the floating joint 45 may have a function of allowing the lid 42 to also swing along the width direction, it is more preferable that the floating joint 45 supports the lid 42 so as to only swing (pivot) along the front and rear direction. That is, the floating joint 45 is arranged with its rotation axis being substantially parallel to the axis of ration of the support unit 43. When the lid 42 is rigidly fixed to the body 41, the O ring 34 will be squashed from one side by the lid 42 that is pressed against the bottom surface 32a, which causes the O ring 34 to become deformed. On the other hand, when the lid 42 is allowed to swing, the O ring 34 is more likely to be squashed from above with a uniform force, which can lead to, for example, improved airtightness of the sample chamber 30.

The lid 42 is equipped, as a biasing member, with a compression spring 46 for biasing the bottom surface 42a toward the sample chamber 30. In this way, under a condition where the body 41 is fixed by means of the fixture unit 44, the lid 42 is pressed against the bottom surface 32a of the recessed part 32. More specifically, because the lid 42 can squash the O ring 34 without losing a pressing force, any situation where the O ring 34 reverts to its original shape does not occur, which can, in turn, help maintain a favorable intimate contact between the bottom surfaces 32a and 42a. Note that the biasing member for biasing the lid toward the sample chamber 30 is not limited to the compression spring 46 mounted on the lid 42, and may be mounted on the fixture unit 44, a connecting part between the lid 42 and the body 41, or other parts. Alternatively, the body 41 itself may function as the biasing member.

Figure 8:
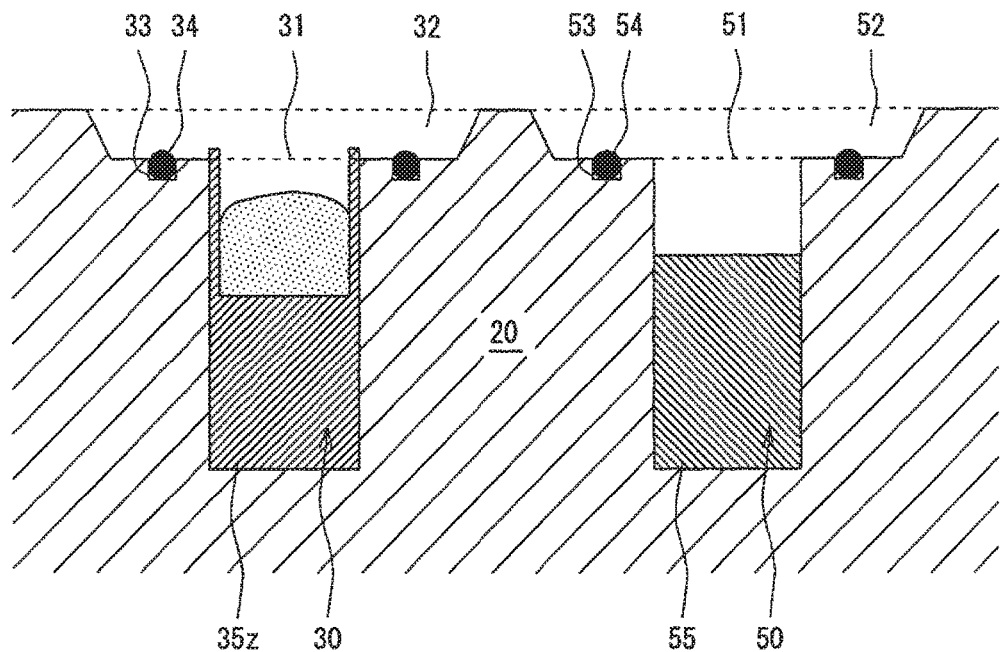
FIG. 8 is a diagram showing, in cross section taken along a width direction, a part of the manifold in the true density measurement device according to the example of the embodiment.

Further referring to FIG. 8, detailed description, in particular, description about the structure of the expansion chamber 50 will be provided below. FIG. 8 is a cross sectional view showing the sample chamber 30 and the expansion chamber 50.

The expansion chamber 50 is a recessed part extending downward from the upper surface of the block 20, and has an internal space in which the capacity changing member 55 can be housed. Preferably, the expansion chamber 50 has, similarly to the sample chamber 30, the shape of a substantially perfect circle in cross section taken along the width direction, and has a diameter which is kept substantially constant in the length direction. The sample chamber 30 and the expansion chamber 50 are preferably disposed as close to each other as possible within a range where operations, such as opening and closing the lids 42 and 56, are not hindered.

As described above, the sample chamber 30 has the variable capacity that can be changed using the sample container 35z. In a case of changing the sample chamber capacity, the capacity of the expansion chamber 50 is preferably changed accordingly (refer to FIG. 10 which will be described below). The expansion chamber 50 can be reduced in capacity through an operator's action of inserting the capacity changing member 55 into the expansion chamber 50.

The diameter, length, and internal space size (capacity) of the expansion chamber 50 may be defined as appropriate based on the capacity of the sample chamber 30 and other factors. In typical devices, the expansion chamber 50 is often designed to have a capacity that is slightly smaller than that of the sample chamber 30. In the case of the true density measurement device 10, because the capacity of the expansion chamber 50 can be easily changed (reduced) using the capacity changing member 55 which is inserted by the operator, the expansion chamber 50 may be designed to have a maximum capacity that is greater than or substantially equal to the maximum capacity of the sample chamber 30. In the case of the true density measurement device 10, the maximum capacity of the expansion chamber 50 is preferably 80~120% or more preferably 90~110% of the maximum capacity of the sample chamber 30. When the maximum capacities of the two chambers are defined to be substantially equal (100±5%), the expansion chamber 50 can be solely used to realize a broader measurement range with a smaller measurement error.

The expansion chamber 50, which is the recessed part formed from the upper surface of the block 20 as described above, is open upward. In other words, an opening 51 of the expansion chamber 50 is defined on the upper surface of the block 20. Then, when the lid 56 is removed, the opening 51 is exposed from the case opening 14a of the case 14. As a result of this, the expansion chamber 50 can be accessed in normal usage conditions, which makes it possible to easily insert and remove the capacity changing member 55. Here, the normal usage conditions represent conditions where the device is ready for true density measurement performed by general operators, and is not being subjected to cleaning, component replacement, maintenance, or inspection.

The expansion chamber 50 is opened or closed by the removable lid 56 in normally usage conditions. The lid 56 is a non-rotary lid of a pushing type similar to the lid 42, but is bolted to the block 20, unlike the lid 42. The lid 56 closes the opening 51 by tightening bolts 58 which have been inserted into (four) bolt holes 57 formed in the block 20. On the circumferential edge region around the opening 51, a recessed part 52 in which the lid 56 is fitted is formed, as in the case of the sample chamber 30. On a bottom surface 52a of the recessed part 52, a groove 53 is formed at a location that surrounds the opening 51, and an O ring 54 is fitted as a sealing member into the groove 53. That is, a mechanism for opening and closing the expansion chamber 50 is similar to that of the sample chamber 30 other than a feature of securing the lid 56 by means of the bolts.

The expansion chamber 50 is open in the same orientation as that of the sample chamber 30. The openings 31 and 51 are arranged side by side on the upper surface of the block 20. For example, the openings 31 and 51 are designed to have substantially the same diameter, and spaced from each other at an interval that is three times the diameter or less, preferably double the diameter or less. The expansion chamber 50 may be open in an orientation that is different from that of the sample chamber 30. In the case of the true density measurement device 10, however, because the expansion chamber 50 is accessed by the operator under normal usage conditions, it is preferable in light of good operability that the openings 31 and 51 are formed on the same plane of the block 20 and located close to each other.

For the capacity changing member 55, there is no specific limitation to its shape and features except for a condition that the capacity changing member 55 can be housed in the expansion chamber 50. Different capacity changing members that vary in capacity may be prepared. It is preferable from the viewpoint of preventing damage to the expansion chamber 50 or other detrimental effects that the capacity changing member 55 is immobilized during measurement. To achieve this, the capacity changing member 55 is preferably formed in the shape of a circular cylinder or a sphere that conforms to the shape of the expansion chamber 50, and has a diameter which is set as close to the diameter of the expansion chamber 50 as possible within the range in which insertion or removal of the capacity changing member 55 is not hampered. In addition, when the sample chamber 30 and the expansion chamber 50 are designed to be substantially identical to each other in the shape and dimensions, such as the diameter, it is possible to use the sample container as a capacity changing member.

Here, the action and effect of the true density measurement device 10 configured as described above are described in detail.

In the true density measurement device 10, because the sample chamber opening and closing mechanism of non-rotary type is employed, a high friction force created by rotation of the lid is not exerted on the O ring 34, which obviates the need to apply the lubricant, such as grease, to the O ring 34. In this way, detrimental effects resulting from the use of grease can be avoided. For example, it is possible to prevent the sample chamber 30 being contaminated by the grease to which the sample 100 or the like adheres, and the accuracy of measurement being deteriorated by counting a volume of the grease, etc.

Further, in the true density measurement device 10, because features for mutual engagement, such as grooves, are absent on any of the side surface 42b of the lid 42, the side surface 32b of the recessed part 32, and other surfaces, it is possible to prevent metallic power being created from metallic components which are rubbing against each other and accordingly worn out. For this reason, contamination and deterioration in airtightness of the sample chamber 30 caused by the metallic powder in a case of using a rotary lid are no longer present.

Still further, in the true density measurement device 10, the capacity of the expansion chamber 50 can be easily changed as well as the capacity of the sample chamber 30. The expansion chamber 50 is open in the same orientation as that of the sample chamber 30, and both of the openings are formed on the upper surface of the block 20. This allows the operator to easily and swiftly change the capacity of the expansion chamber 50 by inserting the capacity changing member 55 into the expansion chamber 50 in a manner similar to insertion of the sample 100 into the sample chamber 30.

Figure 9:
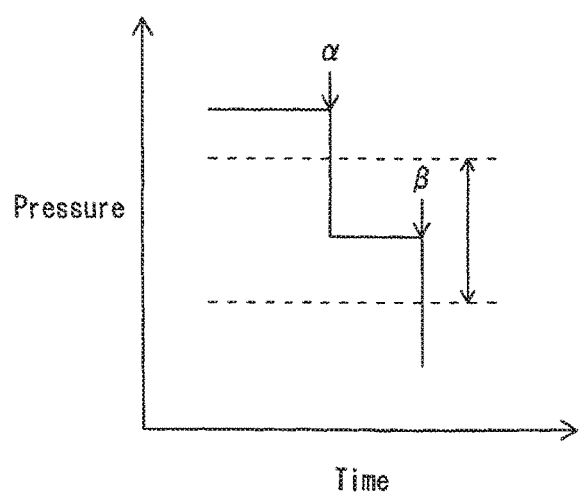
FIG. 9 is a diagram for explaining a function and an effect of the true density measurement device according to the example of the embodiment.
Figure 10:
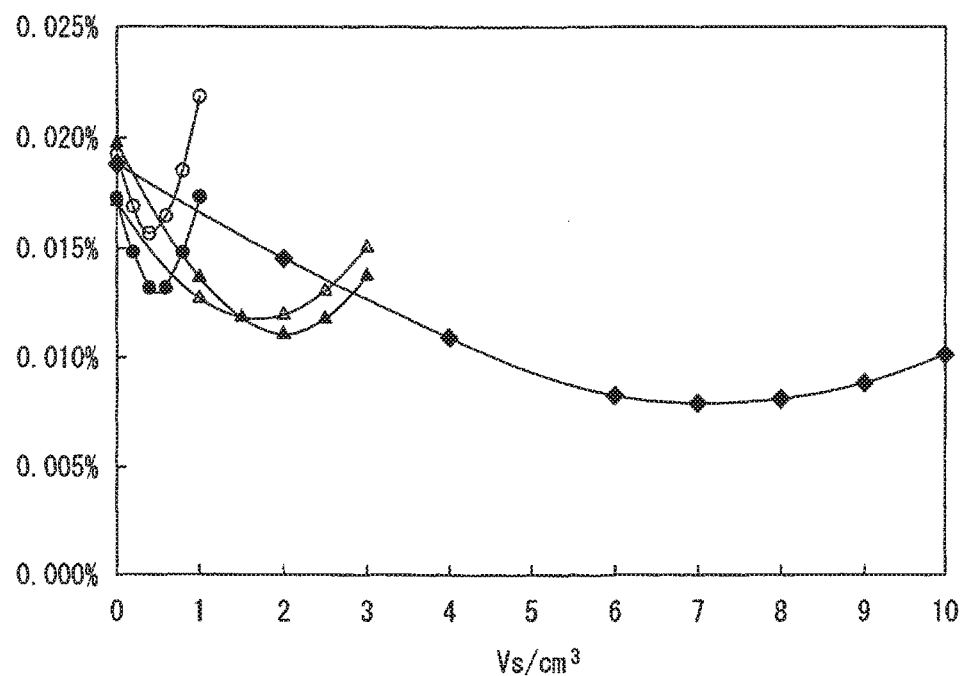
FIG. 10 is a diagram for explaining the function and the effect of the true density measurement device according to the example of the embodiment.

FIGS. 9 and 10 are diagrams for explaining the effect of changing the capacity of the expansion chamber 50. In FIG. 9, an arrow a indicates a point in time when the He gas, which has been introduced in the sample chamber 30, is released into the expansion chamber 50, i.e. when the solenoid valve 25b is opened, and an arrow p indicates a point in time when the He gas is discharged out of the expansion chamber 50, i.e. when the solenoid valve 25c is opened. The release of the He gas into the expansion chamber 50 causes a drop in pressure that is detected by the pressure detector 23. When the drop is too small or too great, a favorable degree of accuracy of measurement cannot be obtained. In other words, there is a range suitable for the drop, or a differential pressure. Because, in the true density measurement device 10, the expansion chamber capacity can be easily changed, it is possible to set the differential pressure within the suitable range, and accordingly improve the accuracy of measurement. For example, when the sample chamber capacity is reduced, the expansion chamber capacity is preferably reduced accordingly. Every time the capacity changing member is replaced, it is desirable to re-calibrate the capacity with the reference sphere.

FIG. 10 shows measurement errors (on a vertical axis) with respect to values of the volume Vs of the sample (on a horizontal axis) obtained when the capacities of the sample chamber 30 and the expansion chamber 50 are changed. In FIG. 10, reference signs ♦ represent an instance of changing a sample chamber capacity Vc to 13.5 ml and an expansion chamber capacity Vr to 13.1 ml, reference signs Δ represent an instance of only changing the sample chamber capacity Vc to 6.0 ml, reference signs ▲ represent an instance of changing the sample chamber capacity Vc to 6.0 ml and the expansion chamber capacity Vr to 5.3 ml, reference signs • represent an instance of only changing the sample chamber capacity Vc to 3.7 ml, and reference signs • represent an instance of changing the sample chamber capacity Vc to 3.7 ml and the expansion chamber capacity Vr to 5.3 ml. When the volume Vs of the sample have values limited to fall within a smaller range, the accuracy of measurement is improved by reducing the sample chamber capacity. Then, when the expansion chamber capacity is reduced in accordance with a reduced sample chamber capacity, the accuracy of measurement is improved more significantly than that in the instance where only the sample chamber capacity is changed. In the true density measurement device 10, for example, the sample chamber 30 and the expansion chamber 50 are defined to have substantially equal maximum capacities, and a measurement is carried out without changing the capacities of the chambers when the volume Vs has greater values, whereas the measurement is carried out after reducing the capacities of the chambers when the volume Vs has smaller values. In this way, the true density of various samples can be measured with a high degree of accuracy using a single device equipped with one expansion chamber.

As described above, the true density measurement device 10 employs, as the opening and closing mechanism for the sample chamber 30, the non-rotary pressing method with which the expansion chamber capacity can be changed through an easy and speedy operation. This can offer noticeable improvement in accuracy of measurement while achieving a reduction in the load of performing maintenance.

Figure 11:
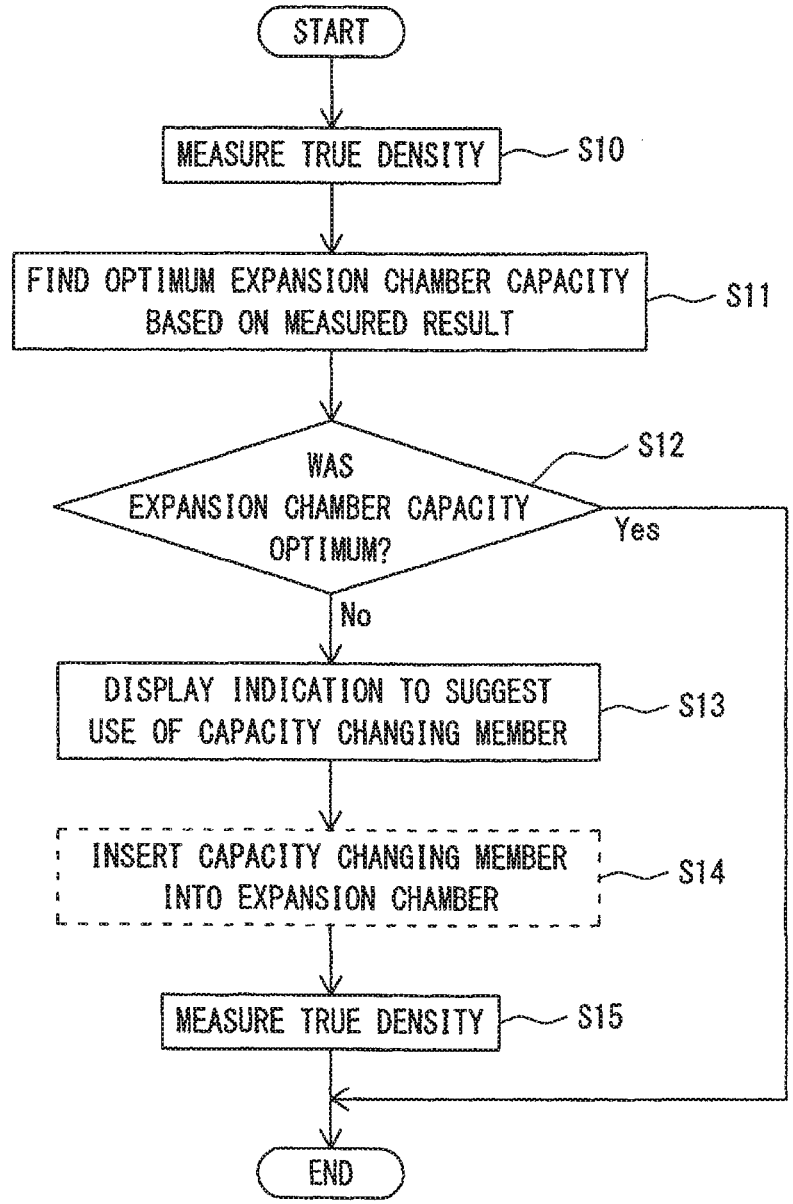
FIG. 11 is a flowchart showing an example of a control mode performed by the true density measurement device according to the example of the embodiment.

Here, an example of a control mode associated with the operation to change the capacity of the expansion chamber 50 in the thus-structured true density measurement device 10 will be illustrated. FIG. 11 is a flowchart representing the control mode.

Firstly, the operator puts the sample 100 into a sample container having an appropriate capacity, and inserts the container into the sample chamber 30. Next, the operator pushes down the body 41 to close the lid 42 of the sample chamber 30 for hermetical sealing. After inputting through the touch panel 13 information, such as the weight of the sample 100, needed to calculate the true density, the operator initiates a measurement. A series of actions to perform true density measurement, such as introduction of the He gas into the sample chamber 30 and release of the He gas into the expansion chamber 50, are automatically performed by a function of the measurement controlling section 12a in the control unit 12. (S10).

Subsequently, based on the measured results in S10, a capacity optimum for the expansion chamber 50 is calculated (S11). More specifically, whether or not the expansion chamber capacity used in S10 is an appropriate condition for reducing the measurement error to a minimum is determined (S12). When it is found, as a result of the determination, that the expansion chamber capacity used in S10 is the appropriate condition for reducing the measurement error to the minimum, the operation mode is finished. On the other hand, when conditions which are more appropriate than the expansion chamber capacity used in S10 are found, i.e. when the expansion chamber capacity used in S10 does not match the expansion chamber capacity calculated in S11, an indication recommending the operator to use the capacity changing member 55 is output to the touch panel 13 (S13). The procedural steps in S11 to S13 are automatically carried out by the function of a notifying section 12b of the control unit 12.

Viewing the indication displayed on the touch panel 13, the operator inserts the capacity changing member 55 into the expansion chamber 50 (S14). When there are two or more capacity changing members, the indication may include specification of a type of the capacity changing members in S13. In this case, the operator selects an appropriate type of capacity changing member and inserts the selected capacity changing member into the expansion chamber 50. Then, the operator restarts the true density measurement (S15).

Meanwhile, the control mode may include a setting to find a capacity optimum for the sample chamber in addition to finding the optimum expansion chamber capacity. Further, the notifying section 12b may recommend the use of the capacity changing member 55 to the operator with, for example, a voice or other methods, rather than displaying the indication on the tough panel 13.

The above-described embodiment may be subjected to design modification as appropriate within a scope that does not impair the object to be achieved by the present invention. For example, the lid 42 may be a separate component isolated from the body 41. To conduct the measurement, the lid 42 is previously fitted into the recessed part 32, and can be pressed down through the body 41, to hermetically seal the sample chamber 30. In this case, the arrangement for guiding the lid 42 to the appropriate position, such as the recessed part 32 or the tapered side surface of the recessed part 32, may be simplified, or even omitted. Separation of the lid 42 and the body 41 offers advantages in that the opening and closing mechanism is simplified, positioning of the lid 42 becomes easier, the lid 42 is cleaned up more easily, etc.

FIGS. 12 to 14C show examples of design modifications. Here, the same components as those of the above-described embodiment are identified by identical reference numerals, and descriptions related to these components will not be repeated.

Figure 12:
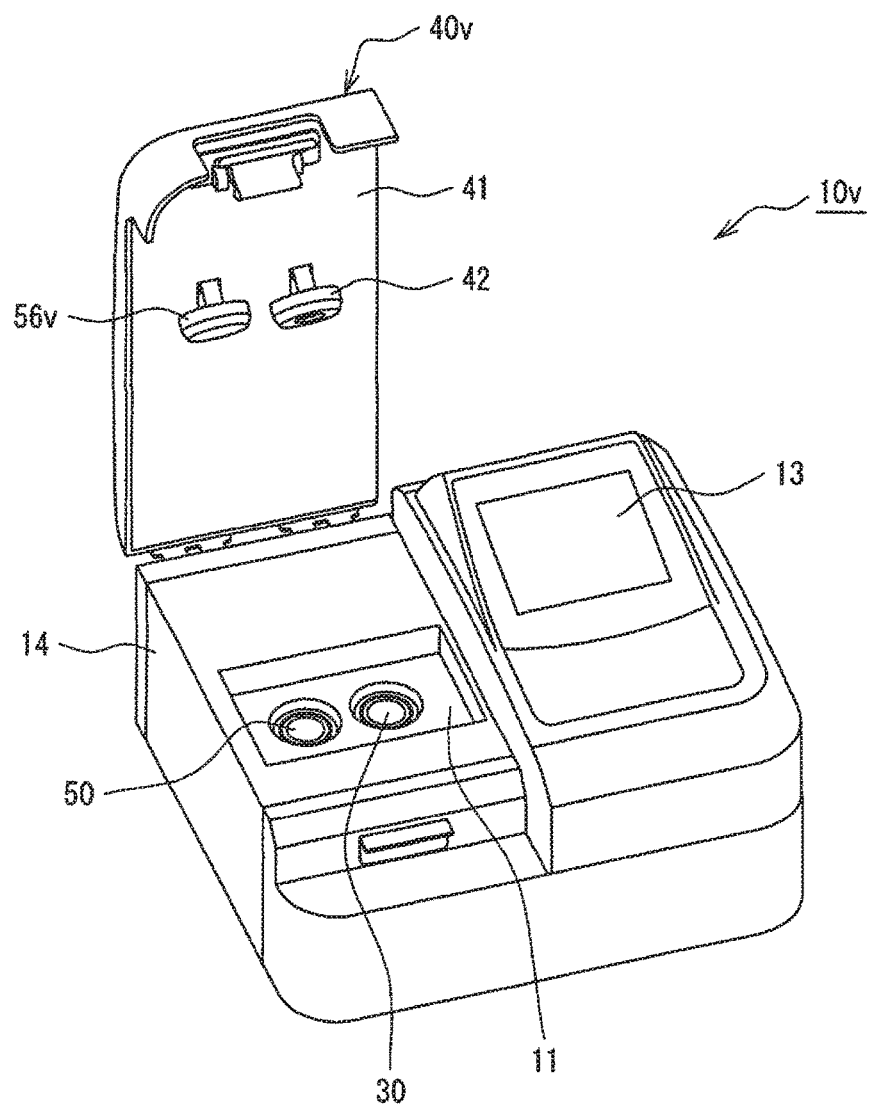
FIG. 12 is a diagram showing a modification of the true density measurement device according to the example of the embodiment.

In a true density measurement device 10v which is shown by way of example in FIG. 12, a lid unit 40v has the body 41 to which, in addition to the lid 42 for the sample chamber 30, a lid 56v for the expansion chamber 50 is also attached, and in this respect, the true density measurement device 10v differs from the true density measurement device 10. The lid 56v is swingably supported, as in the case of the lid 42, between the first and second end parts of the body 41. In this example, when the body 41 is pushed down, the lids 52 and 56v are pressed against corresponding circumferential edge regions around the openings in the chambers, to thereby seal the chambers. In a case where a greater pressing force is needed, the positions of the lids 42 and 56v relative to the body 41 and/or the length of the body 41 may be changed, or a double lever arrangement may be applied to the body 41.

Figure 13:
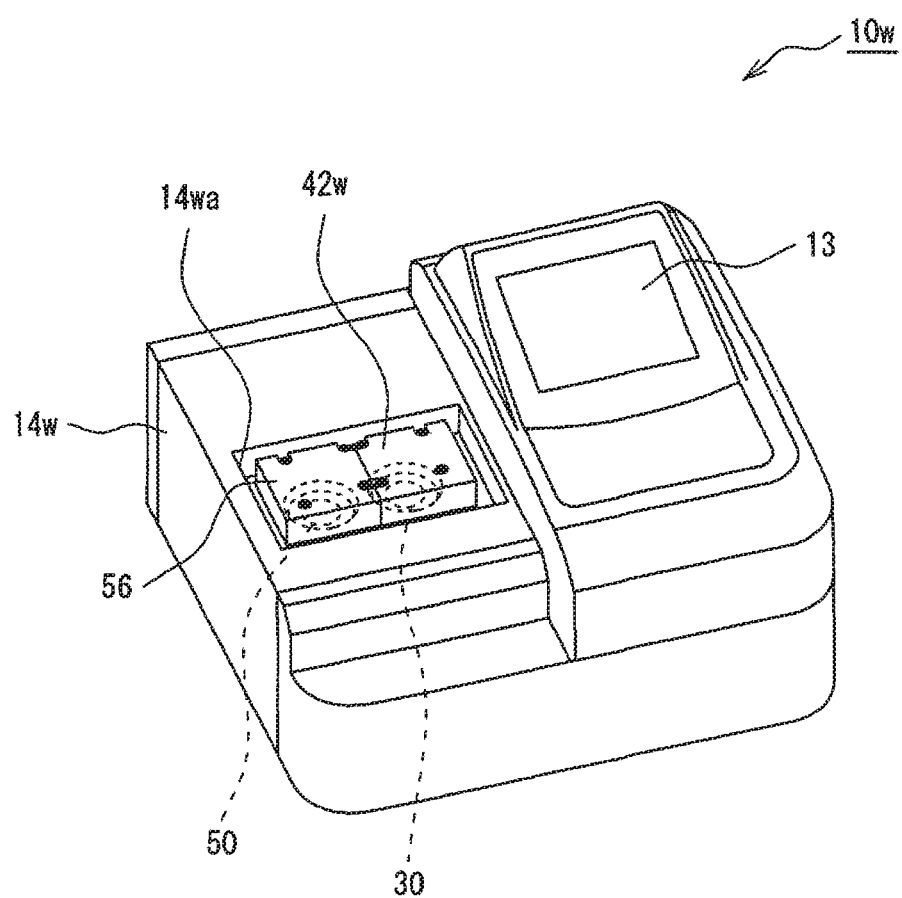
FIG. 13 a diagram showing a modification of the true density measurement device according to the example of the embodiment.

A true density measurement device 10w, which is shown by way of example in FIG. 13, differs from the true density measurement device 10 in that the true density measurement device 10w does not have the body 41, and a lid 42w similar to the lid 56 for the expansion chamber 50 is used for the sample chamber 30. In the true density measurement device 10w, the lids 42w and 56 for closing the chambers are always exposed from a case opening 14wa.

Figure 14A:
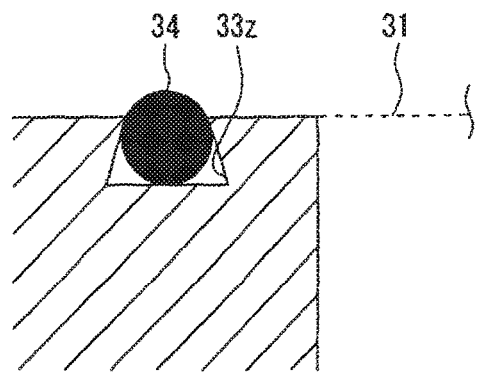
FIG. 14A a diagram showing a modification of the true density measurement device according to the example of the embodiment.
Figure 14B:
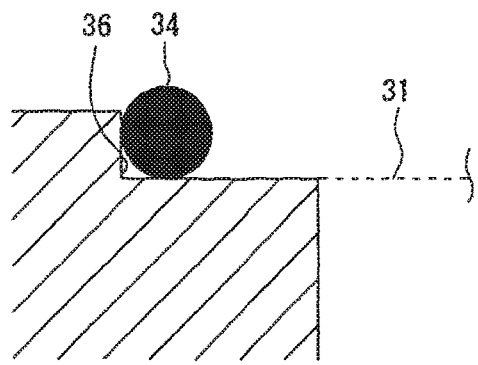
FIG. 14B a diagram showing a modification of the true density measurement device according to the example of the embodiment.
Figure 14C:
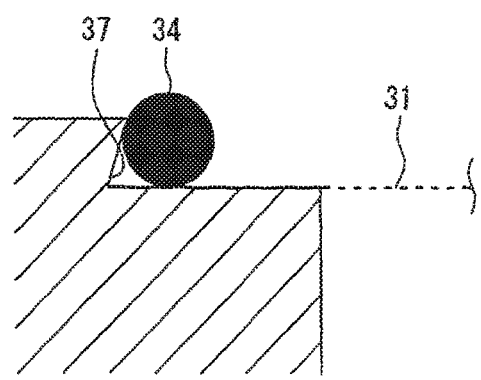
FIG. 14C a diagram showing a modification of the true density measurement device according to the example of the embodiment.

As shown in FIGS. 14A to 14C, a part in which the O ring 34 is fitted does not have to be a groove which is shaped like a letter U in cross section. For example, as shown in FIG. 14A, a groove 33z whose width is diminished upward from the bottom may be formed to prevent the O ring 34 from coming out. The groove 33z is referred to as a dovetail groove. Alternatively, as show in FIGS. 14B and 14C, the circumferential edge region around the opening 31 may be recessed to form a step 36, 37 to which the outer circumference of the O ring 34 is abutted.

REFERENCE SIGN LIST 10, 10v, 10w true density measurement device, 11 manifold, 12 control unit, 12a measurement controlling section, 12b notifying section, 13 touch panel, 14 case, 14a, 14wa case opening, 20 block, 21a, 21b, 21c gas pipe, 22 vent, 23 pressure detector, 24 connector, 25a, 25b, 25c solenoid valve, 26 constant temperature water feeder, 30 sample chamber, 31 opening, 32 recessed part, 32a bottom surface, 32b side surface, 33, 33z groove, 34 O ring, 35, 35z sample container, 36, 37 step, 40, 40v lid unit, 41 lid unit body (body), 42, 42w lid, 42a bottom surface, 42b side surface, 42c recessed part, 43 support unit, 44 fixture unit, 45 floating joint, 46 compression spring, 50 expansion chamber, 51 opening, 52 recessed part, 53 groove, 54 O ring, 55 capacity changing member, 56, 56v lid, 57 bolt hole, 58 bolt, 100 sample.

The invention claimed is:

1. A true density measurement device for measuring a true density of an object to be measured with a gas phase substitution method, the true density measurement device comprising:
    a sample chamber that houses the object to be measured, and is pressurized by introducing an inert gas into the sample chamber;
    an expansion chamber into which the inert gas having been introduced into the sample chamber is released;
    a capacity changing member that can be housed in the expansion chamber; and
    a notifying section that recommends use of the capacity changing member based on a relationship between a previously obtained capacity of the expansion chamber and a measurement error, wherein;
    the expansion chamber is opened and closed by a lid which can be attached or detached under normal usage conditions, and has a variable capacity that is changed by inserting or removing the capacity changing member.

2. The true density measurement device according to claim 1, wherein the expansion chamber is open in an identical orientation to that of the sample chamber.

3. The true density measurement device according to claim 1, further comprising a block in which the sample chamber and the expansion chamber are provided, wherein an opening of the expansion chamber and an opening of the sample chamber are defined on an upper surface of the block.

4. The true density measurement device according to claim 1, wherein the expansion chamber has a maximum capacity that is substantially equal to that of the sample chamber.

* * * * *